(12) United States Patent
Ogawa et al.

(10) Patent No.: US 8,383,027 B2
(45) Date of Patent: Feb. 26, 2013

(54) METHOD OF FABRICATING A TEMPLATE FOR A CONCAVE ARRAY MOLD, A CONCAVE ARRAY MOLD AND A NEEDLE ARRAY SHEET

(75) Inventors: Shotaro Ogawa, Kanagawa (JP); Aya Mochizuki, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/922,387

(22) PCT Filed: Mar. 10, 2009

(86) PCT No.: PCT/JP2009/054504
§ 371 (c)(1),
(2), (4) Date: Oct. 20, 2010

(87) PCT Pub. No.: WO2009/113519
PCT Pub. Date: Sep. 17, 2009

(65) Prior Publication Data
US 2011/0042847 A1 Feb. 24, 2011

(30) Foreign Application Priority Data
Mar. 12, 2008 (JP) ................................. 2008-062825

(51) Int. Cl.
B29C 33/40 (2006.01)
B29C 45/26 (2006.01)
B23P 17/04 (2006.01)
B32B 37/02 (2006.01)

(52) U.S. Cl. ........ 264/219; 264/227; 425/385; 425/588; 29/428; 156/60

(58) Field of Classification Search .................. 264/219, 264/227; 425/588; 29/428; 156/60
See application file for complete search history.

(56) References Cited

U.S. PATENT DOCUMENTS

| | | | | |
|---|---|---|---|---|
| 2,924,863 | A * | 2/1960 | Chavannes | 164/104 |
| 6,663,820 | B2 | 12/2003 | Arias et al. | |
| 6,692,680 | B2 * | 2/2004 | Lee et al. | 264/485 |
| 7,109,819 | B2 * | 9/2006 | Schilling et al. | 333/24 R |
| 7,195,732 | B2 * | 3/2007 | Umeki | 264/496 |
| 7,442,029 | B2 * | 10/2008 | Lof | 425/389 |
| 7,824,584 | B2 * | 11/2010 | Kawaguchi et al. | 264/1.33 |

(Continued)

FOREIGN PATENT DOCUMENTS

| | | |
|---|---|---|
| CA | 2330207 | 8/2005 |
| CA | 2436207 | 12/2008 |
| EP | 2047882 | 4/2009 |
| EP | 1086214 | 11/2009 |
| JP | 54-060360 | 5/1979 |
| JP | 2001-137972 | 5/2001 |

(Continued)

OTHER PUBLICATIONS

International Search Report, PCT/JP2009/054504, Jun. 16, 2009.

*Primary Examiner* — Joseph Del Sole
*Assistant Examiner* — Nahida Sultana
(74) *Attorney, Agent, or Firm* — Young & Thompson (57) ABSTRACT

A method of fabricating a template (14) for a concave array mold (30) having a plurality of recesses of a high aspect ratio includes arranging a plurality of needles (10) in a mutually separated state and fixing the plurality of the arranged needles (10). This method allows a template for a concave array mold having a high aspect ratio structure to be easily and inexpensively fabricated. Further, the thus fabricated template can be used to easily and inexpensively fabricate a concave array mold. Furthermore, a needle array sheet can be fabricated by injecting and fixing a resin solution into the concave array mold (30) and separating the cured resin solution from the concave array mold (30).

2 Claims, 9 Drawing Sheets

U.S. PATENT DOCUMENTS

| | | | | |
|---|---|---|---|---|
| 2001/0003384 A1* | 6/2001 | Morita | | 264/219 |
| 2002/0133129 A1 | 9/2002 | Arias et al. | | |
| 2002/0138049 A1 | 9/2002 | Allen et al. | | |
| 2004/0146611 A1 | 7/2004 | Arias et al. | | |
| 2006/0091584 A1* | 5/2006 | Lyapko | | 264/237 |
| 2006/0131784 A1* | 6/2006 | Sugimoto | | 264/293 |
| 2007/0090567 A1* | 4/2007 | Hwang | | 264/293 |
| 2007/0191761 A1 | 8/2007 | Boone et al. | | |
| 2009/0017276 A1* | 1/2009 | Hoglund et al. | | 428/206 |
| 2010/0072661 A1* | 3/2010 | Cho et al. | | 264/219 |
| 2010/0155988 A1* | 6/2010 | Keil et al. | | 264/219 |

FOREIGN PATENT DOCUMENTS

| | | |
|---|---|---|
| JP | 2002-517300 | 6/2002 |
| JP | 2004-526581 | 9/2004 |
| JP | 2006-264288 | 10/2006 |
| JP | 2006-341089 | 12/2006 |
| JP | 2007-523771 | 8/2007 |
| WO | WO99/64580 | 12/1999 |
| WO | WO02/072189 | 9/2002 |
| WO | WO2005/082596 | 9/2005 |
| WO | WO2008/013282 | 1/2008 |

* cited by examiner

METHOD OF FABRICATING A TEMPLATE FOR A CONCAVE ARRAY MOLD, A CONCAVE ARRAY MOLD AND A NEEDLE ARRAY SHEET

TECHNICAL FIELD

The present invention relates to a method of fabricating a template for a concave array mold having a high aspect ratio structure, a method of fabricating a concave array mold using the template fabricated by the fabrication method, a method of fabricating a needle array sheet using the concave array mold fabricated by the fabrication method, and the template and the concave array mold fabricated by those methods.

BACKGROUND ART

Recently, much attention has been paid to a functional sheet on whose surface a high aspect ratio structure such as a microneedle is formed.

In the medical technology field, there is proposed a needle array sheet on whose surface microneedles, which are needle-like protrusions, are formed as a percutaneous sheet for effectively administering medicaments to a human body through skin. The percutaneous sheet is required to administer medicaments to a human body without causing pain, and thus the microneedle is preferably narrow, has a high aspect ratio, and makes the tip as sharp as possible.

The needle array sheet can be fabricated by cast molding, injection molding, or the like, using a concave array mold in which a needle-like recess, which is a reversed shape of a microneedle, is formed. In general, the concave array mold having a needle-like recess is fabricated by transfer-molding using a template on which a needle-like protrusion is formed, but the template can be fabricated by the following method.

For example, Patent Documents 1 to 3 disclose methods of dry-etching a substrate through a resist pattern formed on a substrate surface.

Patent Document 4 discloses a method of cutting or grinding a metal substrate using a diamond tool.

Further, Patent Document 5 discloses a method of fabricating a transfer mold such as an epoxy resin having a protrusion, using a master mold in which a recess is formed on a metal fine particle dispersed polymer film by laser processing.

Patent Document 1: National Publication of International Patent Application No. 2002-517300
Patent Document 2: National Publication of International Patent Application No. 2004-526581
Patent Document 3: Japanese Patent Application Laid-Open No. 2006-341089
Patent Document 4: National Publication of International Patent Application No. 2007-523771
Patent Document 5: Japanese Patent Application Laid-Open No. 2006-264288

DISCLOSURE OF THE INVENTION

Problems to be Solved by the Invention

Each of the methods disclosed in Patent Documents 1 to 5 is to form needle-like protrusions on a template by microfabricating a single material by dry etching, cutting or grinding, or laser processing. Therefore, the most advanced processing technique is needed to form a needle-like protrusion having a high aspect ratio. For this reason, the fabrication cost per template becomes very high. In addition, a template is damaged as the template is repeatedly used. In general, a plurality of templates is required to be prepared, which causes a problem with a further increase in fabrication cost.

Moreover, according to the methods disclosed in Patent Documents 1 to 5, needle-like protrusions and the base bearing the needle-like protrusions are integrally formed. For this reason, even if some of the needle-like protrusions of the template are deteriorated (deformed, worn, etc.), the entire template needs to be replaced, which also causes a problem with an increase in fabrication cost.

Further, the template material suitable for processing by the methods disclosed in Patent Documents 1 to 4 is hard and fragile like silicon, which also causes a problem with a possibility that the template is broken as the template is repeatedly used.

In view of the above circumstances, the present invention has been made, and an object of the present invention is to provide a template fabrication method of easily and inexpensively forming a template for a concave array mold having a high aspect ratio structure, a concave array mold fabrication method of easily and inexpensively forming a concave array mold, and a needle array sheet fabrication method using the concave array mold fabricated by the fabrication method.

Means for Solving the Problems

An aspect of the present invention relates to a method of fabricating a template for a concave array mold having a plurality of recesses of a high aspect ratio, the template fabrication method including arranging a plurality of needles in a mutually separated state, and fixing the plurality of the arranged needles.

According to the fabrication method according to this aspect, the template is fabricated by arranging and fixing a plurality of needles in a mutually separated state and thus the template on which needle-like protrusions having a high aspect ratio are formed can be easily and inexpensively fabricated.

Moreover, even if some of the needles are deteriorated as the template is repeatedly used, only the deteriorated needles need to be replaced but the entire template hardly needs to be replaced and thus the running cost can be suppressed. Even if the entire template needs to be replaced, the template can be fabricated again at low cost.

Further, high-strength metal needles can be used as the needles constituting a template and thus the template which is hardly broken even after repeated use can be fabricated.

The template fabrication method may fix a plurality of needles by inserting the plurality of needles into an elastic base.

By doing this, the needles can be fixed to the base by the elasticity thereof.

The template fabrication method may be to fix the plurality of needles by bonding a plurality of tapes to whose adhesive surface at least one needle is adhesively fixed.

In this case, it is easy to fabricate a template on which a desired density and number of needles are arranged and fixed by specifying the pitch of needles adhesively fixed to the adhesive surface, the length of the tape, and the number of tapes to be bonded. In addition, it is also possible to fabricate a template on which needles are orderly arranged by bonding a plurality of tapes considering the adhesively fixed position of needles on each tape.

The template fabrication method may be to fix the plurality of needles by bundling the plurality of needles so as to be mutually closed.

In this case, it is easy to fabricate a template on which the needles are orderly arranged by using self arrangement of needles.

The template fabrication method may be to fix the plurality of needles by inserting the plurality of needles into a base in which a plurality of holes are provided.

The template fabrication method may be such that the diameter of the plurality of needles is equal to or greater than 50 μm and equal to or less than 200 μm.

Another aspect of the present invention relates to a method of fabricating a concave array mold having a plurality of recesses, the method including: a template fabrication step of fabricating a template by the template fabrication method; a curing step of curing a mold resin solution in a state in which at least the plurality of needles of the template is immersed in the mold resin solution; and a separation step of separating the mold resin solution cured in the curing step from the template.

The concave array mold fabrication method may be such that the mold resin solution contains a silicone resin.

The concave array mold can be easily separated from the template without causing damage to the concave array mold by using the mold resin solution containing a silicone resin with excellent separatability.

In the concave array mold fabrication method, the curing step may be to cure the mold resin solution in a state in which only the plurality of needles of the template is immersed in the mold resin solution.

Since only the needles of the template are immersed in the mold resin solution, the shape of a needle-like recess of the concave array mold can be specified by a meniscus shape of the mold resin solution. Here, the meniscus shape of the mold resin solution depends on a contact angle of the mold resin solution to the needle. Therefore, the needle-like recess of the concave array mold can be formed into a desired shape by adjusting the contact angle of the mold resin solution to the needle.

In particular, the meniscus shape of the mold resin solution can be formed into a recessed shape near the needle by increasing the contact angle of the mold resin solution to the needle to more than 90°. When the mold resin solution is cured in this state, a concave array mold having a needle-like recess with a rounded root portion can be fabricated. When the needle array sheet is separated from the concave array mold, the concave array mold having a needle-like recess with a rounded root portion can relax stress concentration in the microneedle root portion and thus can prevent the microneedle from being broken. Further, the use of this concave array mold allows a microneedle having a rounded root portion to be formed and thus can prevent the microneedle from being damaged by an external force after the fabrication of the needle array sheet.

The concave array mold fabrication method may be such that a depth of the recess of the concave array mold is equal to or greater than 300 μm and equal to or less than 2000 μm.

Still another aspect of the present invention relates to a needle array sheet fabrication method including: a resin injection step of injecting a resin solution into a sheet fabrication mold including at least one concave array mold fabricated by the fabrication method; a resin curing step of curing the resin solution injected in the resin injection step; and a separation step of separating the resin solution cured in the resin curing step.

The needle array sheet fabrication method may be such that the sheet fabrication mold includes a plurality of the concave array molds.

Advantage of the Invention

Each aspect of the present invention can facilitate template fabrication by arranging and fixing a plurality of needles in a mutually separated state, and thus can easily and inexpensively fabricate a concave array mold or a needle array sheet having a high aspect ratio.

DESCRIPTION OF SYMBOLS

10 Needle
12 Base
14 Template
20 Mold resin solution
22 Mold resin solution tank
24 Surface
30 Concave array mold 32 Needle-like recess
34 Root portion
40 Resin solution
42 Needle-like array sheet
44 Microneedle

BEST MODE FOR CARRYING OUT THE INVENTION

Hereinafter, based on the accompanying drawings, embodiments of the present invention will be described.

FIGS. 1A to 1F each illustrate a process until a needle array sheet according to an embodiment of present invention is fabricated.

Figure 1A:
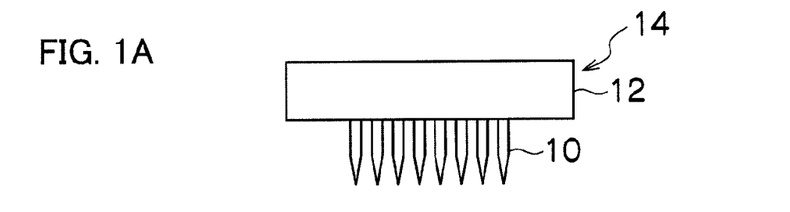
FIG. 1A illustrates a process (1) until a needle array sheet according to an embodiment of present invention is fabricated.

As illustrated in FIG. 1A, first, a step (template fabrication step) starts with fabrication of a template 14 to which a plurality of needles 10 are fixed. A specific fabrication method of the template 14 is described later, but for example, the template 14 can be fabricated by inserting needles 10 in a mutually separated state into a base 12 and fixing the needles 10 to the base 12.

The needles 10 may be various needles regardless of its material as long as the material has a sufficient rigidity. For example, an inexpensive metal pin or needle available on the market such as an insect pin, a marking pin, and an acupuncture needle may be used as the needle 10. Moreover, the cross-sectional shape of the needle 10 is not particularly limited, but may be various cross-sectional shapes such as a circle, an ellipse, and a polygon represented by a triangle, a quadrangle, and a pentagon.

Figure 2:
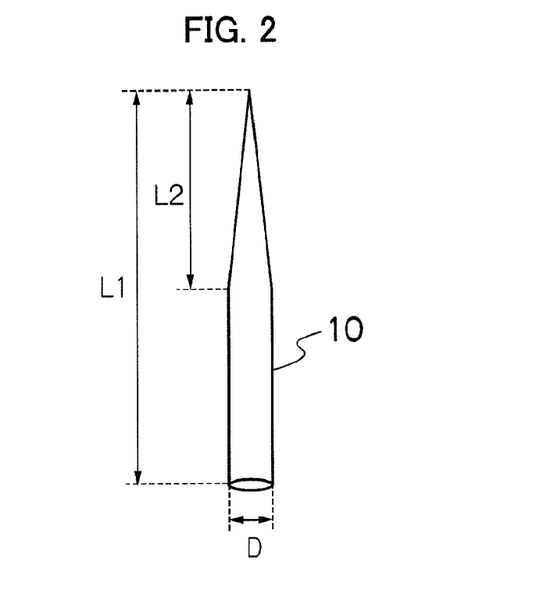
FIG. 2 illustrates a structure of a template fabrication needle having a circular cross section.

FIG. 2 illustrates a template fabrication needle having a circular cross section.

The entire length L1 of the needle 10 may be long enough to fix the needle 10 to the template 14 to be fabricated. The length L2 of an apical end of the needle 10 whose diameter changes continuously may be of any length according to the shape of a microneedle 44 (illustrated in FIG. 1F) which is desired to be formed finally.

The diameter D (needle thickness) of the needle 10 is preferably equal to or greater than 50 μm from the point of view of sufficiently securing the needle strength of the microneedle 44 of the needle array sheet 42 (illustrated in FIG. 1F) to be fabricated. Meanwhile, the diameter D of the needle 10 is preferably equal to or less than 200 μm from the point of view of reducing the burden on a patient by sufficiently thinning the microneedle 44.

Figure 1B:
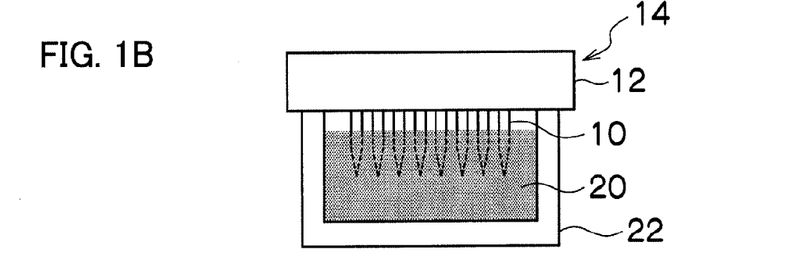
FIG. 1B illustrates a process (2) until a needle array sheet according to an embodiment of present invention is fabricated.

Then, as illustrated in FIG. 1B, in a state in which the needles 10 of the template 14 are immersed in a mold resin solution 20 contained in a mold resin solution tank 22, the mold resin solution 20 is cured (mold resin curing step). Note that the entire template may be immersed in the mold resin solution.

As the mold resin solution 20, it is preferable to use a solution containing resin with excellent demoldability. For example, a silicone resin with a curing agent added to PDMS (polydimethylsiloxane, such as SYLGARD 184 from Dow Corning Toray Co., Ltd., Japan) can be used. The use of the silicone resin with excellent demoldability can improve the separatability of the cured mold resin solution 20 in a later described mold separation step and thus can prevent damage in a concave array mold 30 at mold separation.

Figure 1C:
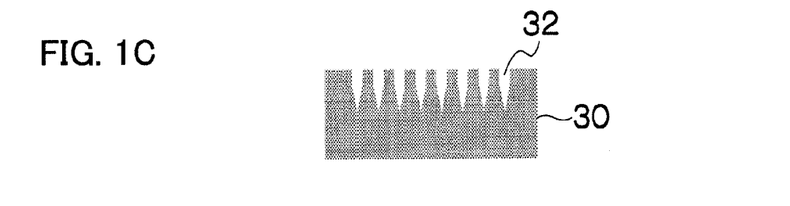
FIG. 1C illustrates a process (3) until a needle array sheet according to an embodiment of present invention is fabricated.

Then, as illustrated in FIG. 1C, the concave array mold 30 having needle-like recesses 32 is fabricated by separating the cured mold resin solution 20 from the template 14 and the mold resin solution tank 22 (mold separation step).

The depth of the needle-like recesses 32 of the concave array mold 30 can be adjusted by changing the depth of the needles 10 immersed in the mold resin solution 20 in the mold resin curing step.

The depth of the needle-like recesses 32 of the concave array mold 30 is preferably equal to or greater than 300 μm from the point of view of efficiently administering medicaments to a patient by sufficiently lengthening the microneedle 44. Meanwhile, the depth of the needle-like recesses 32 is preferably equal to or less than 2000 μm from the point of view of sufficiently securing the strength of the microneedle 44.

Figure 1D:
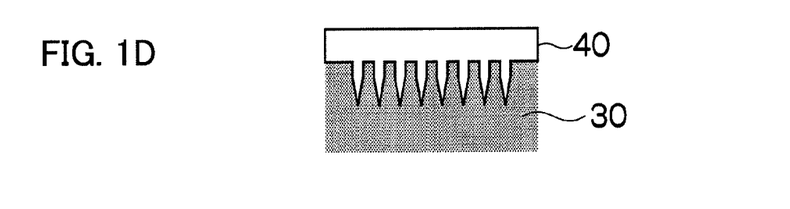
FIG. 1D illustrates a process (4) until a needle array sheet according to an embodiment of present invention is fabricated.

Then, as illustrated in FIG. 1D, a resin solution 40 is injected into the concave array mold 30 obtained in the mold separation step (resin injection step). Examples of the method of injecting the resin solution 40 into the concave array mold 30 include application using a spin coater and dripping using a dispenser.

As the resin solution 40, there can be used a polymer solution obtained by dissolving powder polymer such as gelatin, agarose, pectin, gellan gum, carrageenan, xanthane gum, alginic acid, and starch into a solvent such as warm water. The powder polymer is preferably prepared at a concentration of 10 to 20% by weight depending on the material. Note that as the solvent, there may be used various liquid having volatility, and alcohol other than warm water can also be used. Note that an appropriate amount of medicament may be added to the resin solution 40.

Figure 1E:
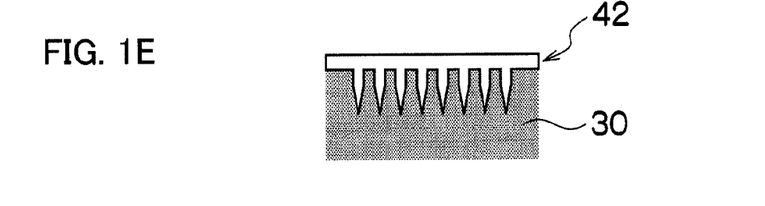
FIG. 1E illustrates a process (5) until a needle array sheet according to an embodiment of present invention is fabricated.

Then, as illustrated in FIG. 1E, a needle array sheet 42 is obtained by curing the resin solution 40 injected into the concave array mold 30 (resin curing step). Examples of the method of curing the resin solution 40 include a method of dry-curing the resin solution 40 by spraying warm air and a method of gelatinizing the resin solution 40 by spraying cold air with low humidity.

Figure 1F:
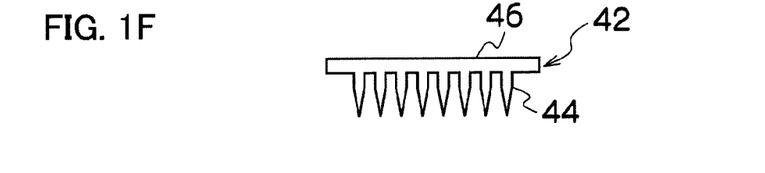
FIG. 1F illustrates a process (6) until a needle array sheet according to an embodiment of present invention is fabricated.

Then, as illustrated in FIG. 1F, the needle array sheet 42 is separated from the concave array mold 30 (sheet separation step).

According to the steps illustrated in FIGS. 1A to 1F as described above, the needle array sheet 42 having the microneedles 44 with a high aspect ratio structure can be fabricated.

Now, a specific aspect of the template fabrication step illustrated in FIG. 1A will be described. As already described, in the template fabrication step, the template 14 is fabricated by curing the needles 10 in a mutually separated state. Hereinafter, a specific aspect of the method of fabricating the template 14 will be described.

Figure 3A:
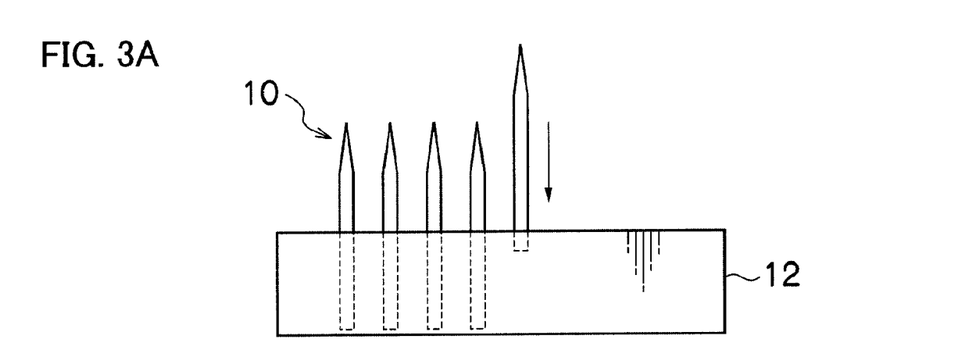
FIG. 3A illustrates a first template fabrication method.
Figure 3B:
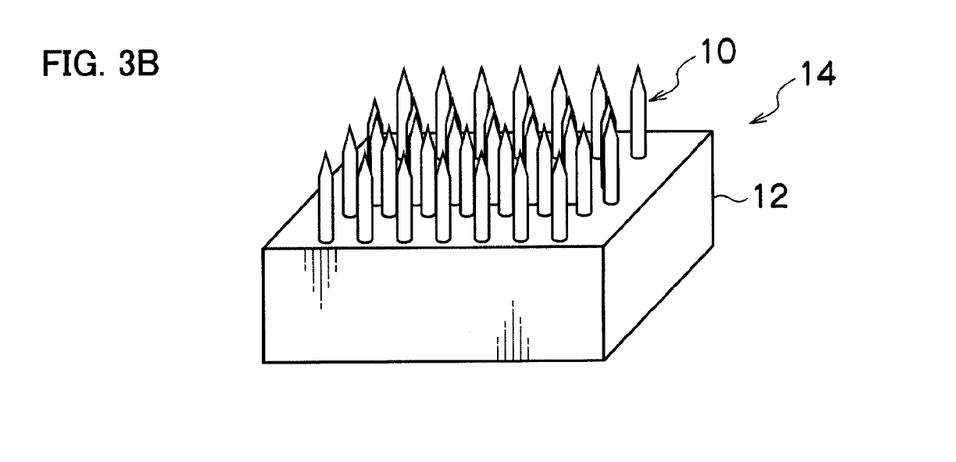
FIG. 3B is a perspective view illustrating a template fabricated by the first template fabrication method.

FIG. 3A illustrates a first template fabrication method. FIG. 3B is a perspective view illustrating a template fabricated by the first template fabrication method.

According to the first template fabrication method, the template 14 is fabricated by inserting the needles 10 in a mutually separated state into the base 12. This method can facilitate fabrication of the template 14 and thus can reduce fabrication costs as well as can improve productivity.

Moreover, the tips of the needles 10 fixed to the base 12 are preferably aligned. The arrangement pattern of the needles 10 are not particularly limited, but the needles 10 can be arranged in various patterns such as a zigzag arrangement and a grid arrangement.

A specific example of the first template fabrication method is to insert the needles 10 to the base 12 made of an elastic member and fix the needles 10 thereto using the elasticity of the base 12.

In addition, another specific example of the first template fabrication method is to insert the needles 10 to the base 12 in which holes are provided in advance and fix the needles 10 to the base 12. When this method is used, the cured needles 10 can be further strengthened by using an adhesive agent together, shrink-fitting the base 12 and the needles 10, or press-fitting the needles 10 with hydraulic pressure.

The diameter of the hole preliminarily provided in the base 12 may be larger than that of the needle 10 or may be smaller than that of the needle 10. For example, when the base 12 is made of a hard material such as metal, it is preferable that the base 12 having a hole with a diameter slightly larger than that of the needle 10 is used to insert the needle 10 into the hole and to be fixed thereto. On the contrary, when the base 12 is made of a material such as resin with a lower hardness than that of the needle 10, it is preferable that the base 12 having a hole with a diameter smaller than that of the needle 10 is used to insert the needle 10 into the hole and to be fixed thereto.

Figure 4A:
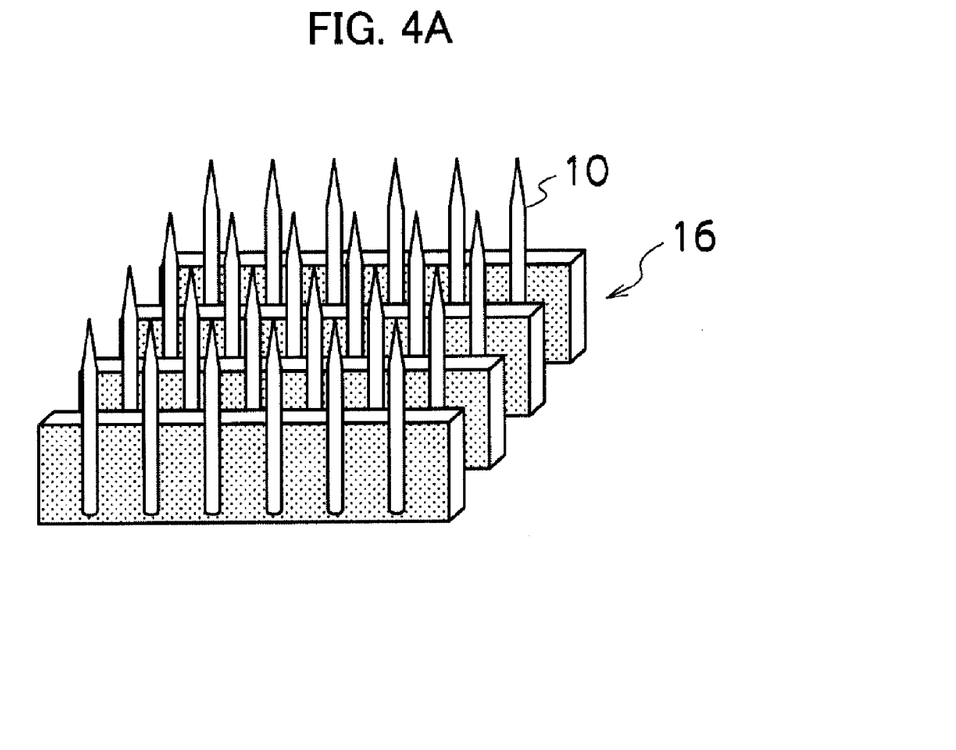
FIG. 4A illustrates a second template fabrication method.
Figure 4B:
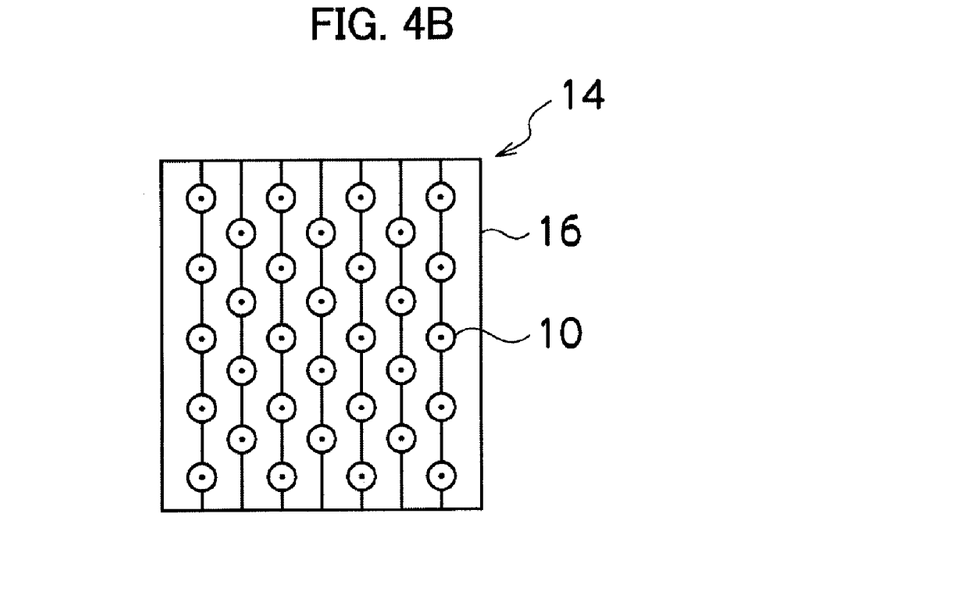
FIG. 4B is a top view illustrating a template fabricated by the second template fabrication method.

FIG. 4A illustrates a second template fabrication method. FIG. 4B is a top view illustrating a template fabricated by the second template fabrication method.

According to the second template fabrication method, the template 14 is fabricated by bonding a plurality of tapes 16 on whose adhesive surface the needles 10 in a mutually separated state are adhesively fixed. This method can facilitate fabrication of the template 14 and thus can reduce fabrication costs as well as can improve productivity. Further, it is easy to fabricate the template 14 on which a desired density and number of needles 10 are arranged and fixed by specifying the pitch of needles 10 adhesively fixed to the tape 16, the length of the tape 16, and the number of tapes 16 to be bonded. In addition, it is also possible to fabricate the template 14 on which the needles 10 are orderly arranged by bonding the tapes 16 considering the adhesively fixed position of the needles 10 on each tape 16.

Figure 5A:
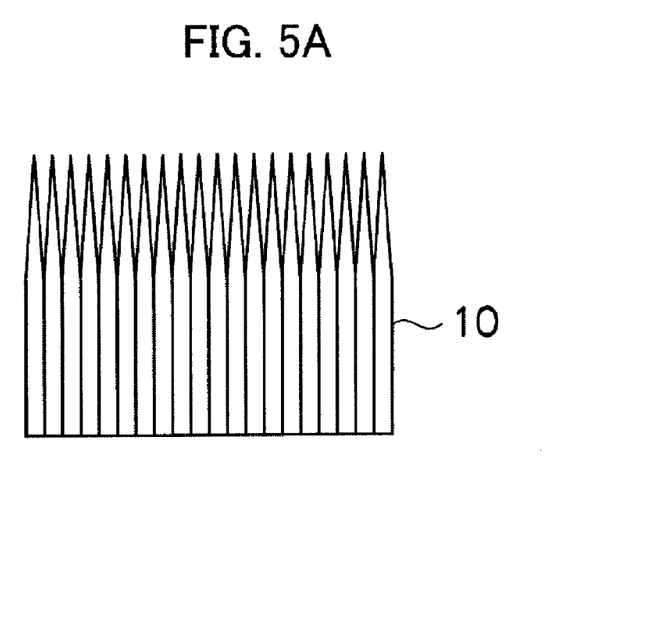
FIG. 5A illustrates a third template fabrication method.
Figure 5B:
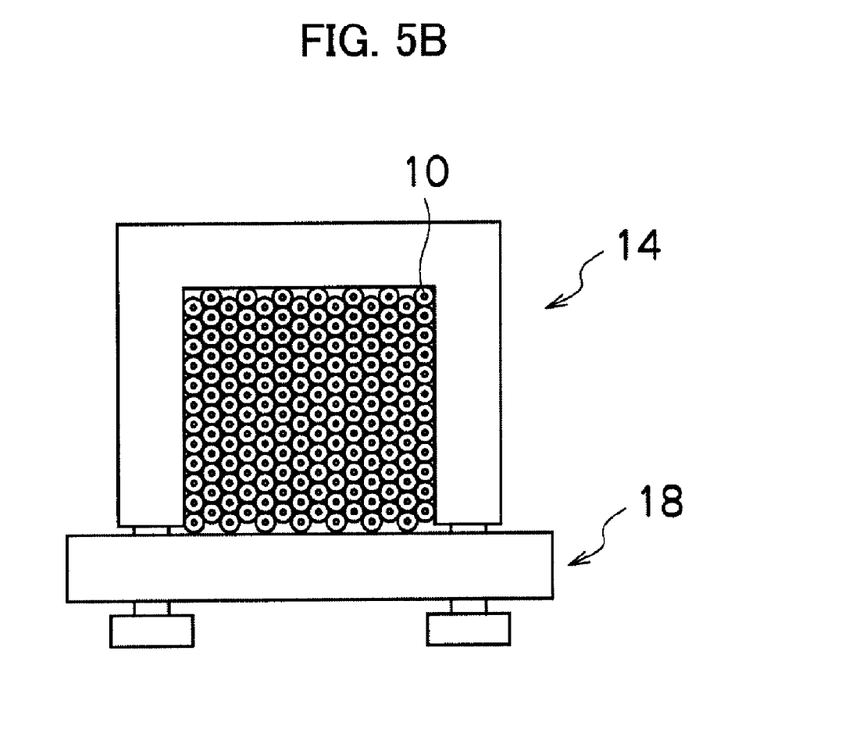
FIG. 5B is a top view illustrating a template fabricated by the third template fabrication method.

FIG. 5A illustrates a third template fabrication method. FIG. 5B is a top view illustrating a template fabricated by the third template fabrication method.

According to the third template fabrication method, the needles 10 in a mutually separated state are bundled so as to be mutually closed. The method of bundling the needles 10 is not particularly limited as long as the needles 10 can be tightened not to fall off, but a jig 18 illustrated in FIG. 5B may be used to bundle the needles 10. This method can fix the needles 10 in an easy and reliable manner and thus can reduce fabrication costs as well as can improve productivity.

Moreover, according to the third template fabrication method, the pitch of the adjacent needles 10 is determined by the diameter D (illustrated in FIG. 2) of the needle 10. Therefore, the pitch and density of the microneedles 44 can be adjusted with high accuracy by fabricating the template 14 using the needles 10 each having an appropriate diameter D.

Further, the needles 10 can be self-arranged in a desired pattern by forming the bottom shape of the needles 10 into various shapes such as a circle, an ellipse, and a polygon represented by a triangle, a quadrangle, and a pentagon.

Figure 6A:
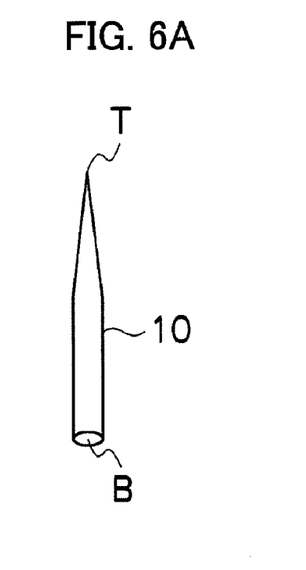
FIG. 6A is a perspective view illustrating a needle having a circular bottom shape.
Figure 6B:
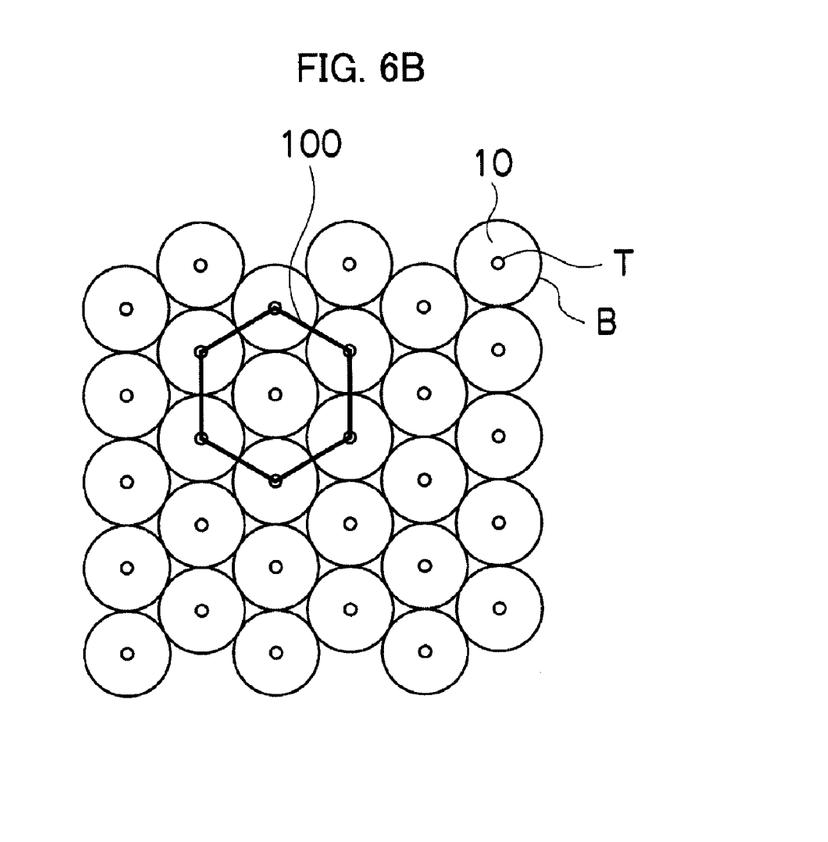
FIG. 6B illustrates a self-arranged pattern of needles when each needle having a circular bottom shape is used.

FIG. 6A is a perspective view illustrating a needle having a circular bottom shape. FIG. 6B illustrates a self-arranged pattern of needles when each needle having a circular bottom shape is used.

When the needles 10 each having a circular bottom surface B illustrated in FIG. 6A are tightened and fixed by the jig 18 (illustrated in FIG. 5B), the needles 10 are orderly self-arranged as illustrated in FIG. 6B. In this manner, when the shape of the bottom surface B of the needle 10 is circular, the self-arranged pattern of the needles 10 becomes a pattern such that needles 10 is adjacent to six needles 10, and the tips T of the six needles 10 forms a regular hexagon 100.

Figure 7A:
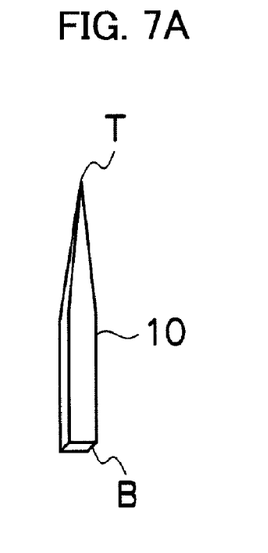
FIG. 7A is a perspective view illustrating a needle having a square bottom shape.
Figure 7B:
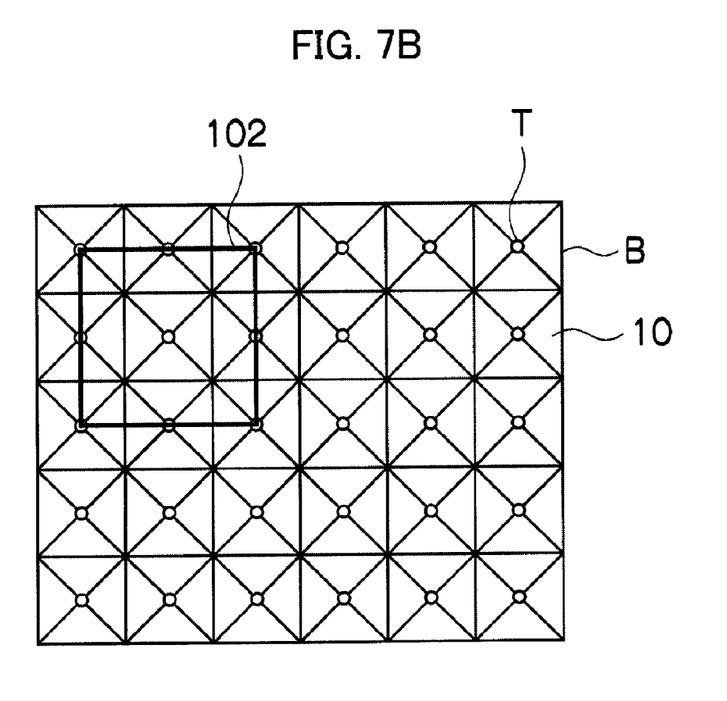
FIG. 7B illustrates a self-arranged pattern of needles when each needle having a square bottom shape is used.

FIG. 7A is a perspective view illustrating a needle having a square bottom shape. FIG. 7B illustrates a self-arranged pattern of needles when each needle having a square bottom shape is used.

When the needles 10 each having a square bottom surface B illustrated in FIG. 7A are tightened and fixed by the jig 18 (illustrated in FIG. 5B), the needles 10 are orderly self-arranged as illustrated in FIG. 7B. In this manner, when the shape of the bottom surface B of the needle 10 is square, the self-arranged pattern of the needles 10 becomes a pattern such that each of the needles 10 is adjacent to four needles 10, and the tips T of the four needles 10 forms a square 102.

Now, a specific aspect of the mold resin curing step illustrated in FIG. 1B will be described.

As already described, in the mold resin curing step, the mold resin solution 20 is cured in a state in which the needles 10 of the template 14 are immersed in the mold resin solution 20. The aspect of immersing the needles 10 in the mold resin solution 20 includes an aspect of immersing the entire template 14 in the mold resin solution 20 and an aspect of immersing a part of the template 14 in the mold resin solution. Hereinafter, a specific aspect of the method of immersing the template 14 will be described.

Figure 8A:
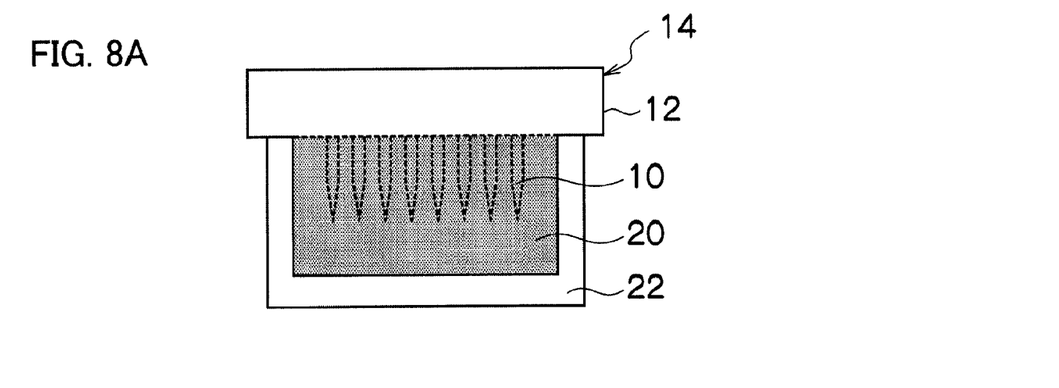
FIG. 8A illustrates a first template immersion method.
Figure 8B:
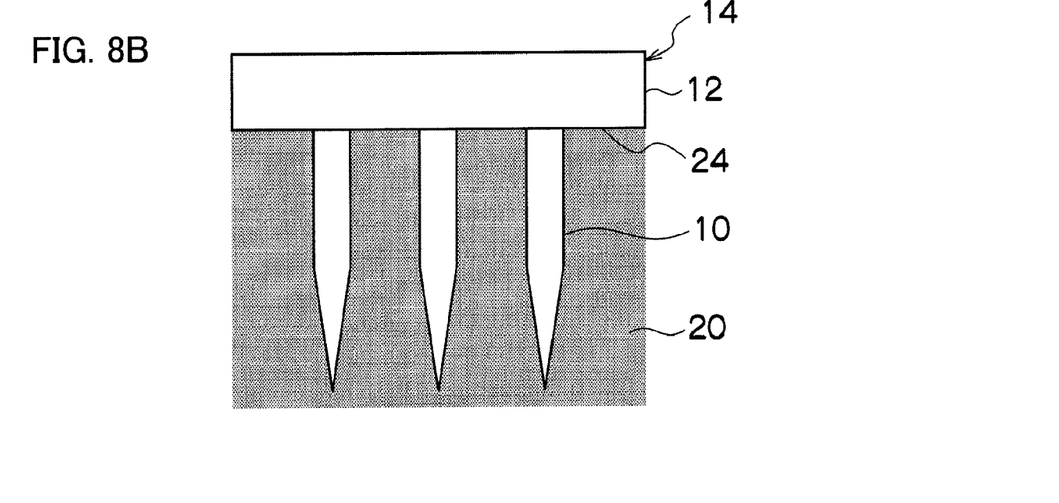
FIG. 8B illustrates a state in which a template is immersed in a mold resin solution by the first template immersion method.
Figure 8C:
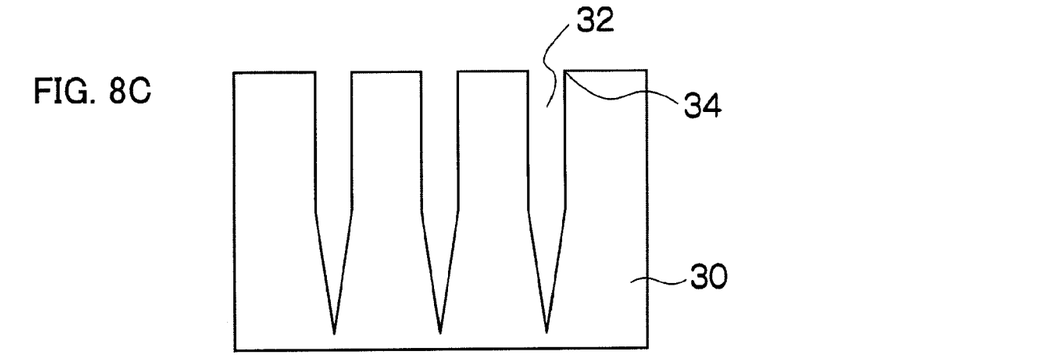
FIG. 8C illustrates a concave array mold fabricated by the first template immersion method.

FIG. 8A illustrates a first template immersion method. FIG. 8B illustrates a state in which a template is immersed in a mold resin solution by the first template immersion method. FIG. 8C illustrates a concave array mold fabricated by the first template immersion method.

According to the first template immersion method, the template 14 is placed in the mold resin solution tank 22 such that the needles 10 and the base 12 are in contact with the mold resin solution 20. According to the first template immersion method, the depth of the needles 10 to be immersed in the mold resin solution 20 can be easily adjusted by the length of the portion of the needles 10 exposed from the base 14.

Moreover, according to the first template immersion method, the mold resin solution 20 is in contact with the surface of the base 12. Therefore, in the mold resin curing step, the mold resin solution 20 can be cured without being affected by a swing of the liquid surface of the mold resin solution 20. Accordingly, the concave array mold 30 having a flat surface along the surface of the base 12 can be fabricated as illustrated in FIG. 8C.

However, the needle-like recesses 32 of the concave array mold 30 fabricated by using the first template immersion method do not have a rounded root portion 34. For this reason, in the sheet separation step, the stress is concentrated on the root portion of each microneedle 44 (illustrated in FIG. 1F) and a microneedle 44 may be broken. In view of this, it is preferable to adopt a second immersion method described below.

Figure 9A:
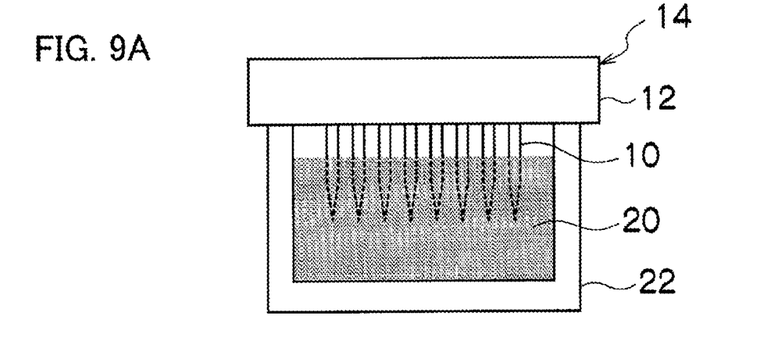
FIG. 9A illustrates a second template immersion method.
Figure 9B:
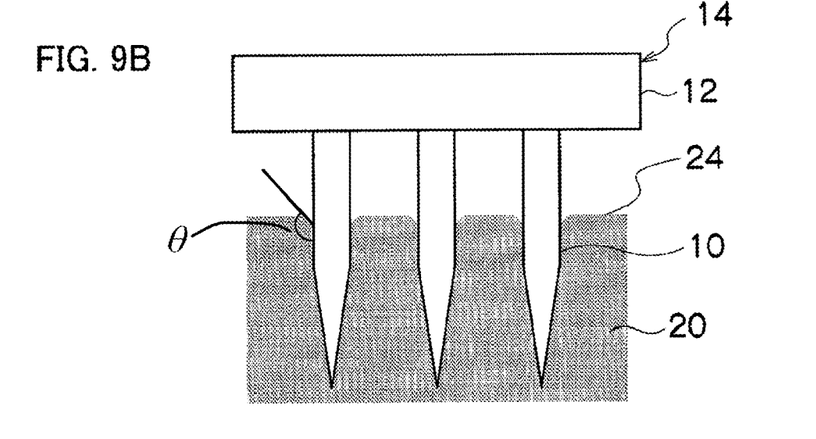
FIG. 9B illustrates a state in which a template is immersed in a mold resin solution by the second template immersion method.
Figure 9C:
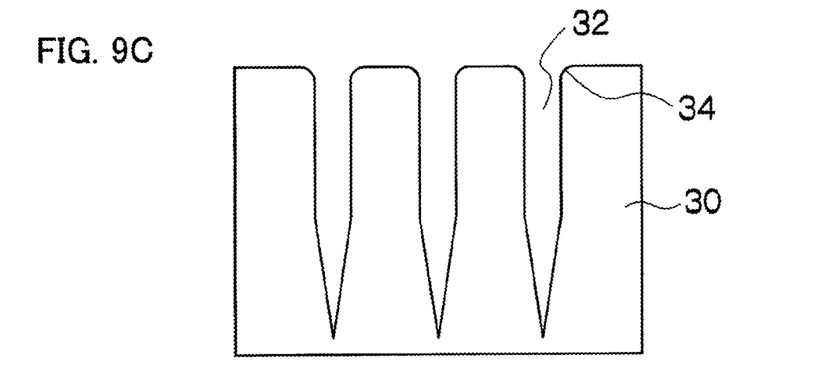
FIG. 9C illustrates a concave array mold fabricated by the second template immersion method.

FIG. 9A illustrates a second template immersion method. FIG. 9B illustrates a state in which a template is immersed in a mold resin solution by the second template immersion method. FIG. 9C illustrates a concave array mold fabricated by the second template immersion method.

In the second template immersion method, the template 14 is placed in the mold resin solution tank 22 such that only a part of the needles 10 including its tips are immersed in the mold resin solution 20. According to the second template immersion method, the surface 24 of the mold resin solution 20 is a free surface. Therefore, the contact angle of the mold resin solution 20 to the needles 10 determines the shape of the surface 24 of the mold resin solution 20, that is, the meniscus shape of the mold resin solution 20. Thus, in the mold resin curing step, the mold resin solution 20 is cured by holding the meniscus shape of the mold resin solution 20 and the concave array mold 30 is fabricated. Accordingly, the concave array mold 30 having the needle-like recesses 32 with the root portion 34 formed into a desired shape can be fabricated by adjusting the contact angle of the mold resin solution 20 to the needles 10.

In particular, the meniscus shape of the mold resin solution 20 can be formed into a recessed shape near the needles 10 as illustrated in FIG. 9B by increasing the contact angle of the mold resin solution 20 to the needles 10 to more than 90°. When the mold resin solution 20 is cured in this state, the concave array mold 30 having the needle-like recesses 32 with an arc-shaped root portion 34 can be formed as illustrated in FIG. 9C. For example, the needle-like recess 32 having the root portion 34 rounded with a curvature radius of about 100 μm can be formed.

In the sheet separation step, the needle-like recesses 32 having the rounded root portions 34 can relax stress concentration in the microneedle root portions of the microneedles 44 (illustrated in FIG. 1F) and thus can prevent the microneedles 44 from being broken.

Further, the use of the concave array mold 30 having the needle-like recesses 32 with rounded root portions 34 allows the microneedles 44 having rounded root portions to be formed. Therefore, the microneedles 44 can be prevented from being damaged by an external force after the fabrication of the needle array sheet 42.

The contact angle of the mold resin solution 20 to the needles 10 may be adjusted by appropriately selecting the material of the needles 10 or the component of the mold resin solution 20 or may be adjusted by performing surface processing on the needles 10. Examples of the method of adjusting the contact angle by performing surface processing on the needles 10 include a method of forming a film having a repellency to the mold resin solution 20 on a surface of the needles 10 by fluorinating the needles 10 (Teflon® coating).

As already described, according to the present embodiment, the template 14 is fabricated by fixing the needles 10 in a mutually separated state. Therefore, the template 14 having the needles 10, which are needle-like protrusions having a high aspect ratio, can be easily and inexpensively fabricated.

Moreover, even if some of the needles 10 are deteriorated as the template 14 is repeatedly used, only the deteriorated needles 10 need to be replaced but the entire template 14 hardly needs to be replaced. Thus, the running cost can be suppressed. Even if the entire template 14 needs to be replaced, the template 14 can be fabricated again at low cost.

Further, high-strength metal needles can be used as the needles 10 of the template 14 and thus the template 14 which is hardly broken even after repeated use can be fabricated.

Hereinbefore, an embodiment of the present invention has been described in detail, but the present invention is not limited to this. It is apparent that various improvements and modifications may be made to the present invention without departing from the spirit and scope of the present invention.

For example, the above embodiment describes an example in which the mold resin solution 20 contains a silicone resin with a curing agent added to PDMS, but the mold resin solution 20 may contain various resins other than the silicone resin. For example, as the mold resin solution 20, there may be used a solution containing a resin such as polystyrene and PMMA (polymethylmethacrylate) dissolved in an organic solvent. In this case, in order to improve separatability of the concave array mold 30, it is preferable to apply a separating agent over the surface of the template 14 before the template 14 is immersed in the mold resin solution 20.

Moreover, the above embodiment describes an example in which the resin solution 40 is injected into one concave array mold 30, but the resin solution 40 may be injected into a large area sheet fabrication mold containing a plurality of concave array molds 30.

Figure 10:
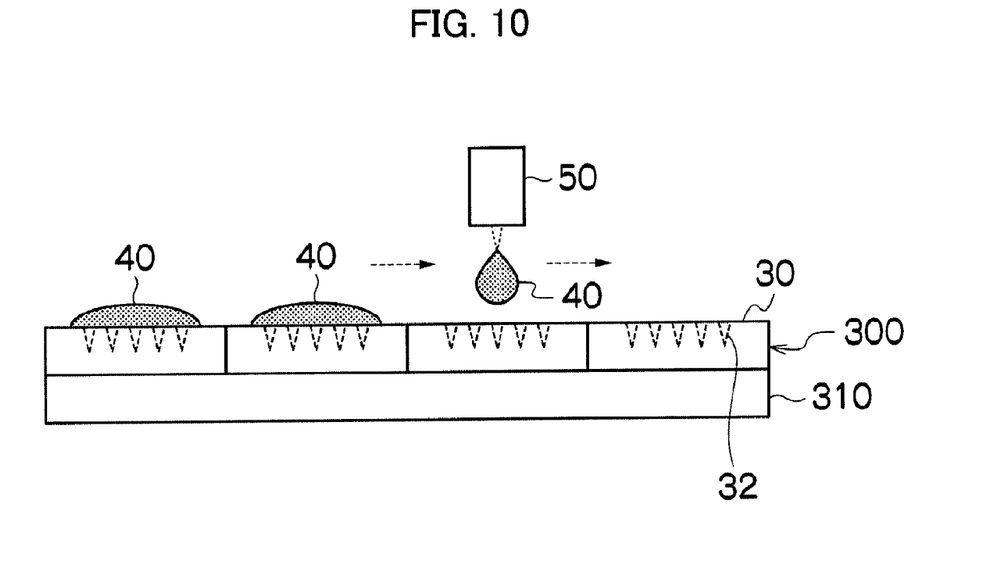
FIG. 10 illustrates a state in which a resin solution is injected into a large area sheet fabrication mold.

FIG. 10 illustrates a state in which a resin solution is injected into a large area sheet fabrication mold. As illustrated in FIG. 10, the resin solution 40 is injected into a large area sheet fabrication mold 300 configured by arranging a plurality of concave array molds 30 side by side on a base substrate 310. As the method of injecting the resin solution 40 into the large area sheet fabrication mold 300, an aspect of dripping the resin solution 40 using a dispenser 50 is preferable. Use of the dispenser 50 allows the resin solution 40 to be selectively injected into a region in which the resin solution 40 is required to be injected.

Note that the above embodiment describes an example of fabricating the needle array sheet 42 having microneedles 44, but the present invention is not limited to this and can be applied to fabrication of various sheets having a high aspect ratio structure such as a micropillar.

EXAMPLES

When an attempt was made to fabricate a needle array sheet based on the method according to the above described embodiment, an excellent needle array sheet was fabricated as described below.

First, the template 14 was fabricated by the method illustrated in FIGS. 3A and 3B. As the needle 10, there was used a metal needle with a diameter of 200 μm and a length of 20 mm. As the base 12, there was used a urethane rubber sheet having a size of 50 mm×50 mm and a thickness of 10 mm. Each root portion of the needles 10 was inserted into the base 12 so as to align the tips of the needles 10. Thereby, the template 14 to which 20×20 needles 10 were fixed was fabricated. The needles 10 were arranged at a 1 mm pitch on the template 14. A portion 3 mm from the needle tip of each needle 10 was exposed from the base 12.

Then, the mold resin solution 20 was prepared. As the mold resin solution 20, there was used SYLGARD 184 (from Dow Corning Toray Co., Ltd., Japan) with a curing agent added thereto. The SYLGARD 184 with a curing agent added thereto was injected in the mold resin solution tank 22 having an internal wall size of 40 mm×40 mm and a depth of 20 mm so as to have a liquid height of 12 mm. Subsequently, the SYLGARD 184 was placed in a vacuum chamber and was subjected to defoaming of the SYLGARD 184 for a few minutes under reduced pressure.

Then, by the method illustrated in FIG. 9A, the template 14 was immersed in the mold resin solution 20. Specifically, the template 14 was placed in the mold resin solution tank 22 in such a manner that the needles 10 of the template 14 were oriented downward and a portion 1000 μm from the tip of each needle 10 was immersed in the SYLGARD 184.

In this state, the mold resin solution 20 was cured and the cured mold resin solution 20 was separated from the template 14. Specifically, the SYLGARD 184 was subjected to thermal processing (at a temperature of 80° C. and for a time of 50 minutes) in an oven and was cured. Subsequently, the SYLGARD 184 was subjected to natural cooling until returned to room temperature. Then, the SYLGARD 184 was separated from the template 14 and the mold resin solution tank 22. Thus, the concave array mold 30 having the needle-like recesses 32 each having a diameter of 200 μm and a depth of 1000 μm was obtained.

Then, the resin solution 40 was prepared. Specifically, gelatin was dissolved into warm water at a temperature of 40° C. to prepare the resin solution 40 with a gelatin concentration of 20% by weight.

The prepared resin solution 40 was dripped on the surface of the concave array mold 30 through the dispenser and was injected by air pressure. Subsequently, warm air at a temperature of 60° C. was sprayed for 120 minutes to dry the resin solution 40.

A PET sheet with a thickness of 100 μm having an adhesive layer was attached to the dry-cured resin solution 40, that is, the rear surface of the needle array sheet 42. Then, the needle array sheet 42 was separated together with the PET sheet from the concave array mold 30. Thus, the needle array sheet 42 having the microneedles 44 with a diameter of 160 μm and a height of 1000 μm was obtained.

The invention claimed is:

1. A method of fabricating a needle array sheet comprising:
   a template fabrication step of fabricating a template by arranging a plurality of needles in a mutually separated state and fixing the arranged plurality of needles;
   a concave array mold fabrication step of fabricating a concave array mold by curing a mold resin solution in a state in which at least the plurality of needles of the template are immersed in the mold resin solution having a contact angle of more than 90 degrees with respect to a root portion of the needle and separating the cured mold resin solution from the template;
   a resin injection step of injecting a resin solution into a sheet fabrication mold including the concave array mold fabricated by the concave array mold fabrication step;
   a resin curing step of curing the resin solution injected in the resin injection step; and
   a separation step of separating the resin solution cured in the resin curing step.

2. The needle array sheet fabrication method according to claim 1, wherein the sheet fabrication mold includes a plurality of the concave array molds.

\* \* \* \* \*